US012661513B2

(12) United States Patent
Papay et al.

(10) Patent No.: US 12,661,513 B2
(45) Date of Patent: Jun. 23, 2026

(54) METHOD FOR ACCESSING THE GLOSSOPHARYNGEAL NERVE

(71) Applicant: The Cleveland Clinic Foundation, Cleveland, OH (US)

(72) Inventors: Francis A. Papay, Westlake, OH (US); Abeer Kalandar, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 178 days.

(21) Appl. No.: 18/388,553

(22) Filed: Nov. 10, 2023

(65) Prior Publication Data

US 2024/0189598 A1      Jun. 13, 2024

Related U.S. Application Data

(60) Provisional application No. 63/424,268, filed on Nov. 10, 2022.

(51) Int. Cl.
*A61N 1/36* (2006.01)

(52) U.S. Cl.
CPC ........ *A61N 1/3611* (2013.01); *A61N 1/36057* (2013.01)

(58) Field of Classification Search
None
See application file for complete search history.

(56) References Cited

U.S. PATENT DOCUMENTS

| | | | | |
|---|---|---|---|---|
| 5,766,248 | A * | 6/1998 | Donovan | ................ A61F 13/36 2/21 |
| 11,857,792 | B2 * | 1/2024 | Elliott | ...................... A61B 5/08 |
| 2009/0112282 | A1 * | 4/2009 | Kast | ................... A61N 1/36071 607/46 |

* cited by examiner

*Primary Examiner* — Mallika D Fairchild
(74) *Attorney, Agent, or Firm* — Fortem IP LLP

(57) ABSTRACT

A method of treating a subject includes an incision step that includes making an incision adjacent to an earlobe of the subject; a dissecting step that includes dissecting anatomical structure of the subject to provide access to a glossopharyngeal nerve of the subject; and a coupling step that includes operatively coupling a neurostimulator to the glossopharyngeal nerve. The dissecting step includes dissecting a stylohyoid muscle and a posterior belly of a digastric muscle of the subject.

20 Claims, 6 Drawing Sheets

METHOD FOR ACCESSING THE GLOSSOPHARYNGEAL NERVE

CROSS-REFERENCE TO RELATED APPLICATIONS

This application claims the benefit of U.S. provisional application Ser. No. 63/424,268 filed Nov. 10, 2022, the contents of which are incorporated by reference.

TECHNICAL FIELD

The present disclosure relates to a method for accessing the glossopharyngeal nerve of a patient and more particularly, a surgical method for accessing and coupling a neurostimulator to the glossopharyngeal nerve for treatment of obstructive sleep apnea.

BACKGROUND

Obstructive sleep apnea (OSA) is a common disorder characterized by recurrent episodes of upper airway collapse during sleep. The pathophysiology of this condition is multifactorial, both anatomic and neurological. For example, inadequate signaling from the hypoglossal nerve causes tongue base collapse, causing upper airway obstruction. Therefore, hypoglossal nerve stimulation has been established in treating OSA patients who cannot tolerate positive airway pressure therapy. Stimulating this nerve produces a protruding, stiffened tongue that opens up the pharyngeal airway. However, hypoglossal nerve stimulation has showed variable results. Some patients still experience airway collapse after hypoglossal nerve stimulation, while others do not have favorable anatomy for the placement of neuromodulator devices at the hypoglossal nerve. Accordingly, an activation system that stimulates other nerves of the lingual system and pharyngeal airway could be helpful to open the airway.

BRIEF SUMMARY OF THE INVENTION

According to a first aspect, a method of treating a subject includes an incision step that includes making an incision adjacent to an earlobe of the subject; a dissecting step that includes dissecting anatomical structure of the subject to provide access to a glossopharyngeal nerve of the subject; and a coupling step that includes operatively coupling a neurostimulator to the glossopharyngeal nerve. The dissecting step includes dissecting a stylohyoid muscle and a posterior belly of a digastric muscle of the subject.

DETAILED DESCRIPTION

The glossopharyngeal nerve and its pharyngeal plexus provide innervation to the stylopharyngeus muscle, pharyngeal constrictors, levator veli palatini, and cricopharyngeus muscles. When the stylopharyngeal muscle is activated in concert with dilation of the pharyngeal constrictor muscles, it moves the pharyngeal wall laterally. Therefore, the glossopharyngeal nerve may be a target for neuromodulation to improve airway obstruction in OSA patients.

Figure 1:
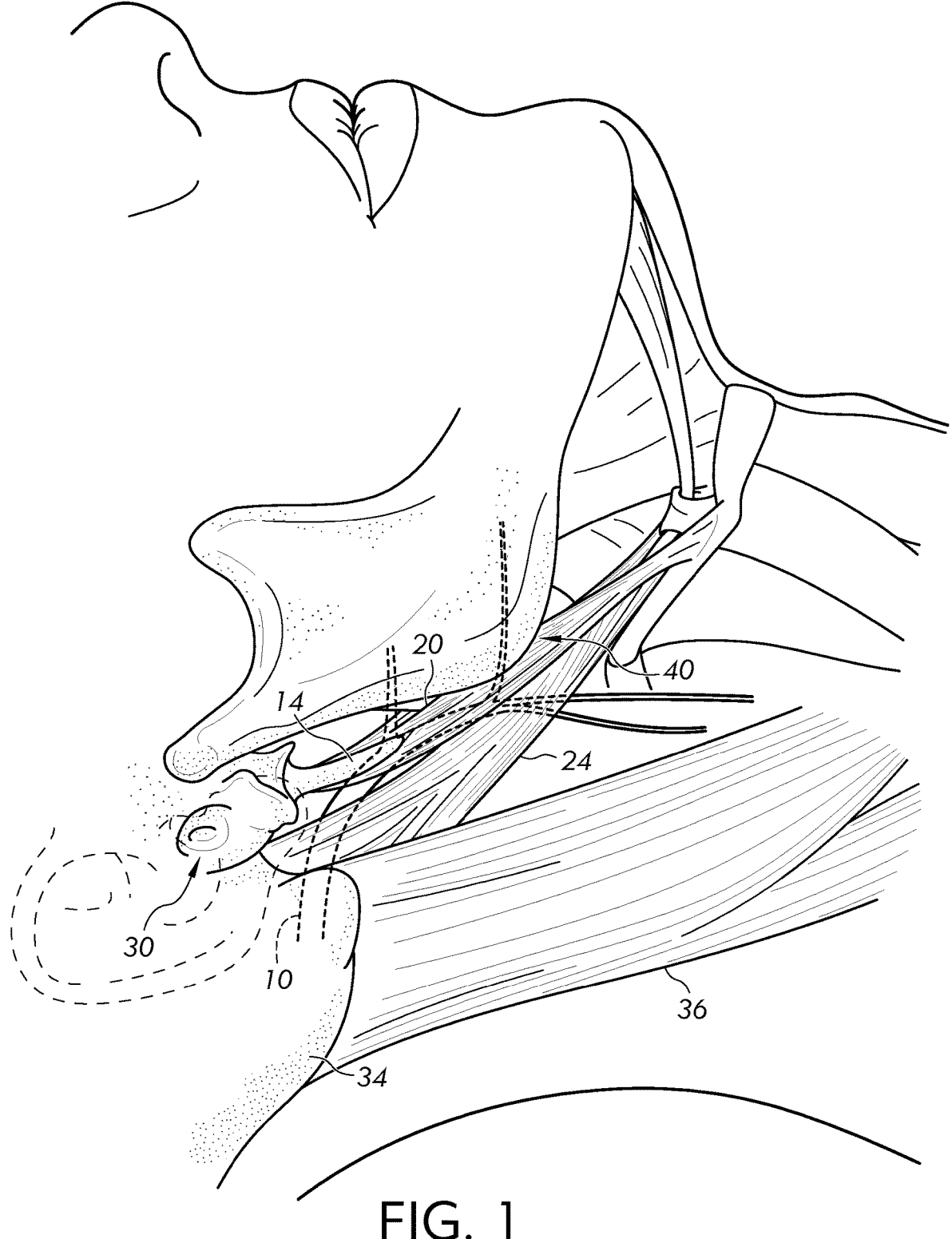
FIG. 1 is an anatomical view of a patient.

FIG. 1 is an anatomical view of a patient showing the glossopharyngeal nerve 10 and its position relative to other anatomical features. In particular, the glossopharyngeal nerve 10 is positioned deep to the styloid process 14, stylohyoid muscle 20, and the posterior belly of the digastric muscle 24. Moreover, the glossopharyngeal nerve 10 is inferior to the external auditory canal 30, anterior to the confluence of the mastoid process 34 and the sternocleidomastoid muscle 36, and deep to a vertex of the mandibular gonial angle 40.

Historically, extracranial approaches to the glossopharyngeal nerve 10 have been attempted to treat conditions such as glossopharyngeal neuralgia, although such approaches were abandoned due to high risk of recurrence and their associated morbidity. Intracranial approaches to the glossopharyngeal nerve were performed until the 1970s, when percutaneous procedures were developed and became an alternative to craniotomies. To this date, there is no surgical approach to the glossopharyngeal nerve for neuromodulation, particularly neuromodulation to treat OSA.

Figure 2:
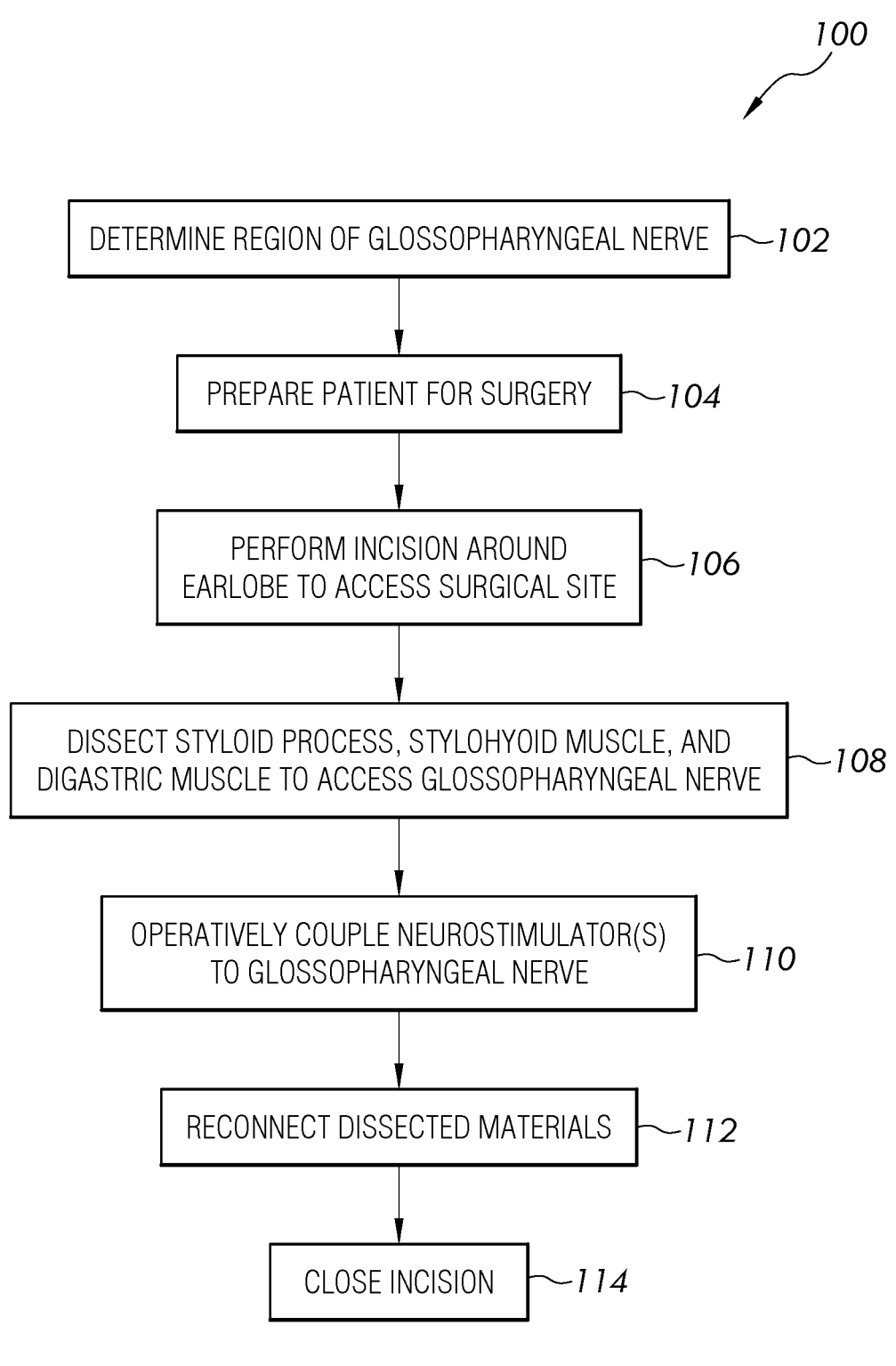
FIG. 2 shows an example method for accessing a glossopharyngeal nerve of the patient.
Figure 3:
FIG. 3 shows the patent after a step of preparing the patient for surgery.
Figure 4:
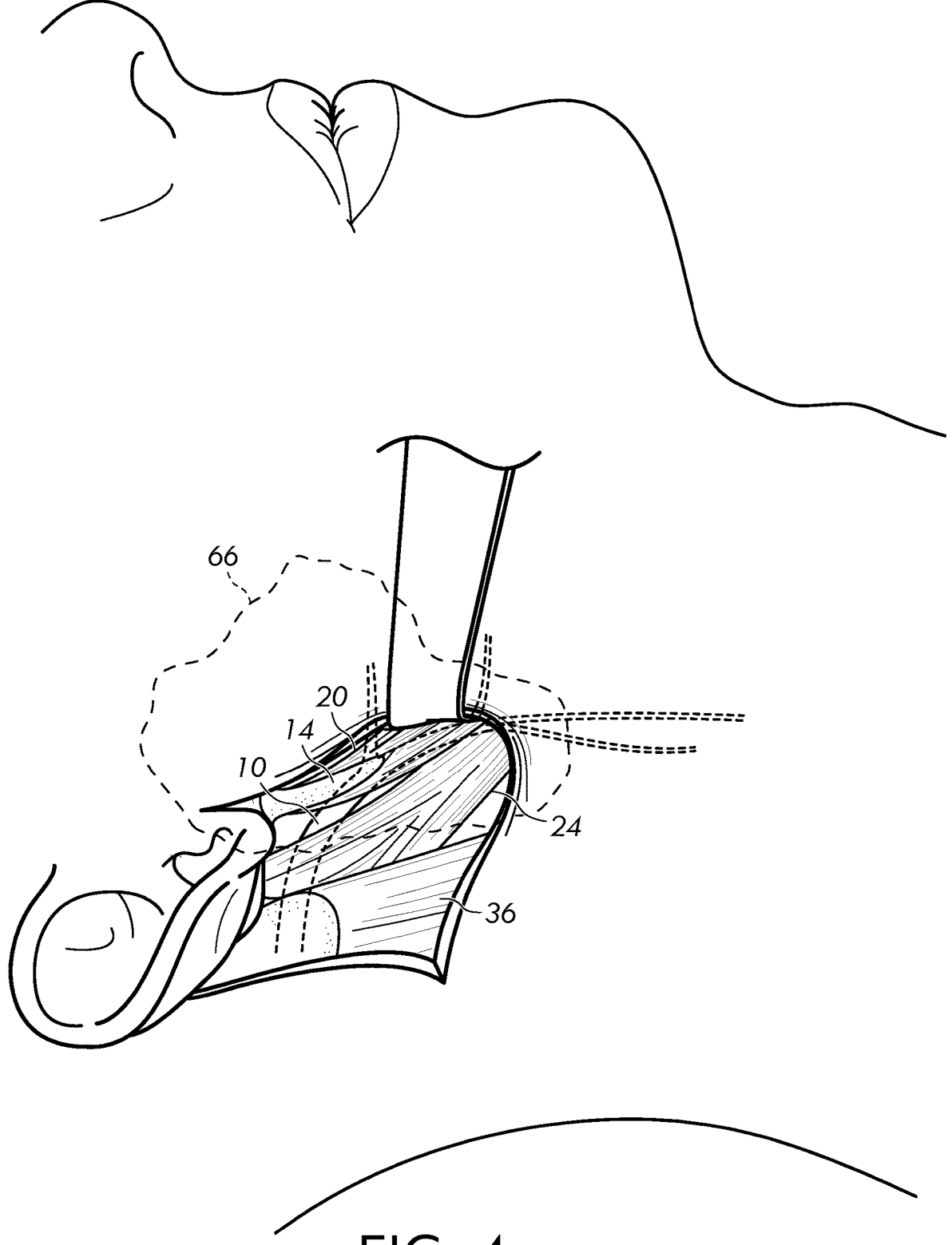
FIG. 4 shows the patient after an incision step of the method.
Figure 5:
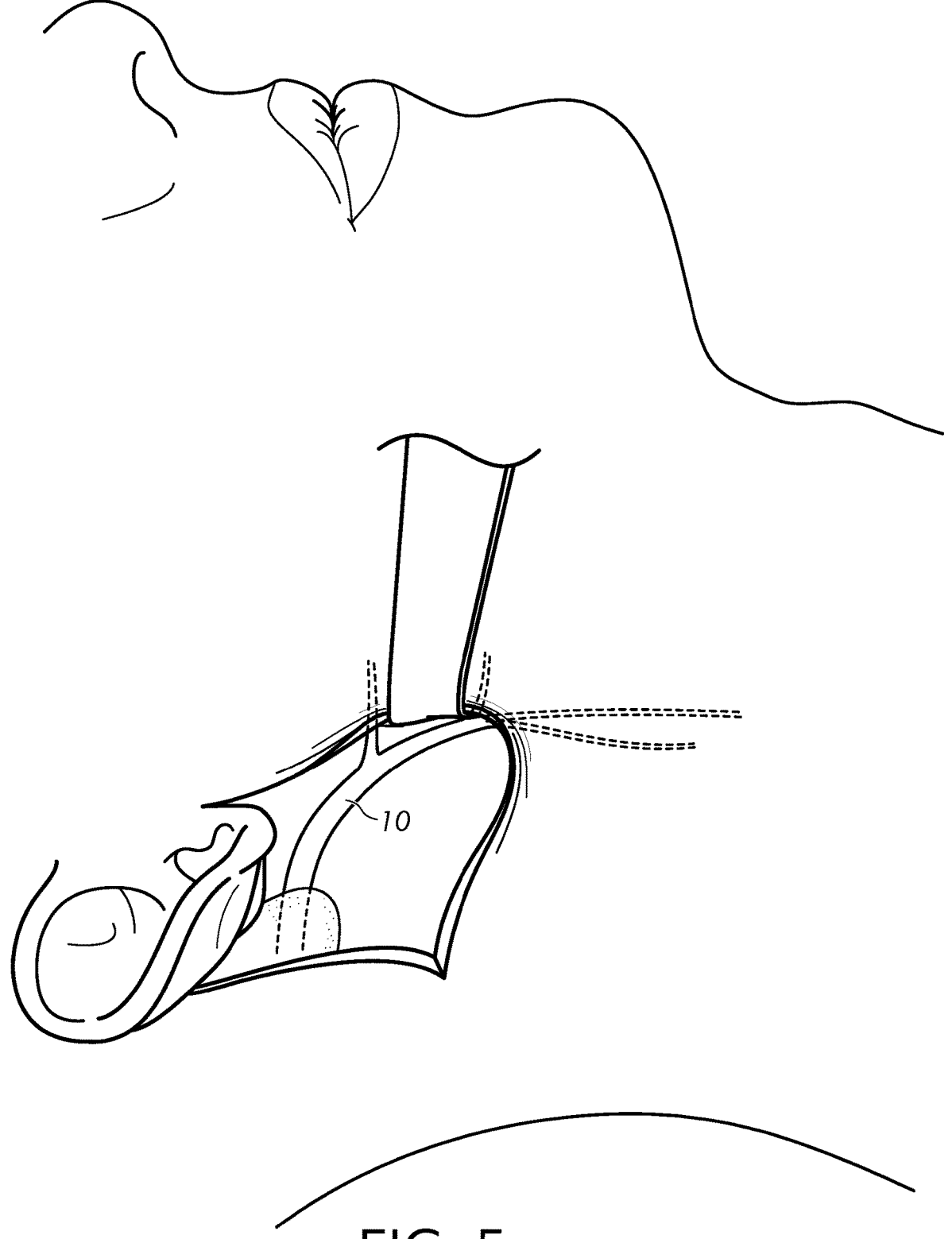
FIG. 5 shows the patient after a dissecting step of the method.

Turning to FIGS. 2-5, an example method 100 for accessing and coupling a neurostimulator to the glossopharyngeal nerve 10 will now be described. FIG. 2 is a flowchart that summarizes various steps of the method 100, while FIGS. 3-5 show the patient at various stages during the method 100.

The method 100 includes an initial step 102 of preoperatively determining a region of the glossopharyngeal nerve 10 for coupling the neurostimulator. The glossopharyngeal nerve 10 is a cranial nerve that exits the brainstem from the sides of the upper medulla, just anterior to the vagus nerve. It leaves the skull through the central part of the jugular foramen, and descends beneath the styloid process 14 to the posterior lower border of the stylopharyngeus muscle 36. It then passes under cover of the hyoglossus muscle and is finally distributed to the palatine tonsil, the mucous membrane of the fauces and base of the tongue, and the serous glands of the mouth.

A neurostimulator can be coupled to a particular region 50 of the glossopharyngeal nerve 10 as shown in FIG. 1. At least one of the following landmarks can be used to determine the region 50: the inferior border of the external auditory canal 30, the confluence of the mastoid process 34 and the sternocleidomastoid muscle 36, and the vertex of the mandibular gonial angle 40. Once the landmark(s) is/are identified, the region 50 of the glossopharyngeal nerve 10 can be determined based on one or more predetermined ranges of distances from the landmark(s).

For example, the region 50 can be defined by a first predetermined range that is around 3.4 cm inferior to the inferior border of the external auditory canal 30; a second predetermined range that is around 1.4 cm anterior to the confluence of the mastoid process 34 and the sternocleidomastoid muscle 36, and/or a third predetermined range that is around 2.2 cm deep to the vertex of the mandibular gonial angle 40. For the purposes of this disclosure, a range is "around" a particular distance from an associated feature if the range is at least that distance minus 0.5 cm and at most that distance plus 0.5 cm from the feature. In one specific example, the first predetermined range is 3.4+/−0.5 cm (i.e., at least 3.1 cm and at most 3.9 cm) inferior to the inferior border of the external auditory canal 30, the second predetermined range is 1.4+/−0.2 cm (i.e., at least 1.2 cm and at most 1.6 cm) anterior to the confluence of the mastoid process 34 and the sternocleidomastoid muscle 36, and the third predetermined range is around 2.2+/−0.3 cm (i.e., at least 1.9 cm and at most 2.5 cm) deep to the vertex of the mandibular gonial angle 40. However, the region 50 can be defined using other ranges and/or landmarks without departing from the scope of the disclosure.

In some examples, the above step 102 of determining the region 50 of the glossopharyngeal nerve 10 can be performed partially or in full by a computer-operated system that is configured to detect the landmark(s) and determine the region 50 accordingly. In particular, the computer-operated system can include one or more imaging systems (e.g., an MRI machine, a CT scanner, an x-ray machine, or combinations thereof) that are operable to detect and map the landmark(s), and a computer processor in communication with the imaging systems that stores the predetermined range(s) and is operable to determine the region of the glossopharyngeal nerve (or a data set corresponding to that region) based on the detected landmark(s) and the predetermined range(s). The computer-operated system can also include a user interface (e.g., display, keyboard, touchscreen, etc.) in communication with the processor that enables a user to provide one or more inputs to the processor and enables the system to provide an output (e.g., image, data set, etc.) corresponding to the determined region 50. For example, the output could be an image of the region 50 or a data set providing boundaries of the region 50.

Coupling a neurostimulator to this focused region 50 of the glossopharyngeal nerve 10 is useful for multiple reasons. For example, the neurostimulator as coupled in this region 50 can be used to stimulate the glossopharyngeal nerve 10 and treat pathologies such as OSA. Moreover, coupling the neurostimulator in this region 50 enables the neurostimulator to be implanted using the surgical method described further below, which is a minimally invasive technique. However, it is to be appreciated that the specific region for coupling the neurostimulator can vary by patient, and can be determined using other ranges and/or landmarks than those described above. Moreover, although the region 50 in the present example is determined pre-operatively, in other examples the region 50 may be determined during surgery once the glossopharyngeal nerve 10 has been accessed.

The method 100 next includes a step 104 of preparing the patient for surgery. As shown in FIG. 3, the patient can be arranged in a supine position with the neck slightly extended and the head turned to the side opposite from the glossopharyngeal nerve 10. Moreover, a marking 62 can be applied to the patient to indicate a path for incision. The marking 62 has a first portion 62a that extends inferiorly around the base of the earlobe, and a second portion 62b that extends inferiorly from the first portion 62a along the posterior border of the sternocleidomastoid muscle 36 (e.g., similar to a facelift incision).

At step 106, an incision can then be performed along the marking 62 to access the surgical site of patient. Specifically, an incision can be made through the subcutaneous tissue and superficial fascia, with care to identify and protect the great auricular nerve. Because the incision is performed along the marking 62, it will have first and second portions that mimic the first and second portions 62a, 6b of the marking 62.

After incision, the skin portions on opposite sides of the incision are retracted relative to each other, thereby exposing the internal anatomy of the patient (see e.g., FIG. 4). For example, the skin portions can be retracted anteriorly.

As shown in FIG. 4, the parotid gland 66 is superficial to the styloid process 14, stylohyoid muscle 20, and digastric muscle 24, which are superficial to the glossopharyngeal nerve 10. Accordingly, the parotid gland 66 can be swept gently anteriorly and superiorly from its regular position to a displaced position, in order to access those deeper elements.

At step 108, the stylohyoid muscle 20 and digastric muscle 24 are dissected to expose the glossopharyngeal nerve 10. More specifically, the stylohyoid muscle 20 and posterior belly of the digastric muscle 24 are first dissected to expose the styloid process 14. For example, an incision can be made through each muscle 20, 24, thereby separating the muscle 20, 24 into two separate portions that are attached at respective ends to the patient but can be retracted relative to each other to expose the styloid process 14. Alternatively, each muscle 20, 24 can be dissected to remove a portion therefrom, while the remaining muscle 20, 24 stays intact and connected at both ends to the patient.

Blunt dissection can then be optionally performed on the styloid process 14 to denude the styloid process 14 and help expose the glossopharyngeal nerve 10. Specifically, layers of tissue on the styloid process 14 are carefully separated and removed (e.g., using fingers or blunt instruments) until the styloid process 14 is substantially bare. This will help visually distinguish the styloid process 14 from its neighboring anatomy, particularly the glossopharyngeal nerve 10. Moreover, in some examples, at least a portion of the styloid process 14 can be broken off from the remaining temporal bone, to help further expose the glossopharyngeal nerve 10. For instance, the entire styloid process 14 is separated from the temporal bone in the present embodiment.

After the dissection step 108, the glossopharyngeal nerve 10 can be exposed as shown FIG. 5). The method 100 then includes a step 110 of operatively coupling one or more neurostimulators to the glossopharyngeal nerve 10. For example, each neurostimulator can include one or more cuff electrodes that are placed around the glossopharyngeal nerve 10, or one or more electrode leads that are arranged adjacent to (e.g., in direct contact with) the glossopharyngeal nerve 10 and substantially fixed in place using hooks that wrap around the glossopharyngeal nerve and/or penetrate into surrounding muscles. In some examples, the electrode(s) of each neurostimulator can simply be lodged between the glossopharyngeal nerve 10 and surrounding anatomy to substantially fix the electrode(s) in place. Preferably, the electrode(s) of each neurostimulator will be located within the previously identified region 50 of the glossopharyngeal nerve 10.

Figure 6:
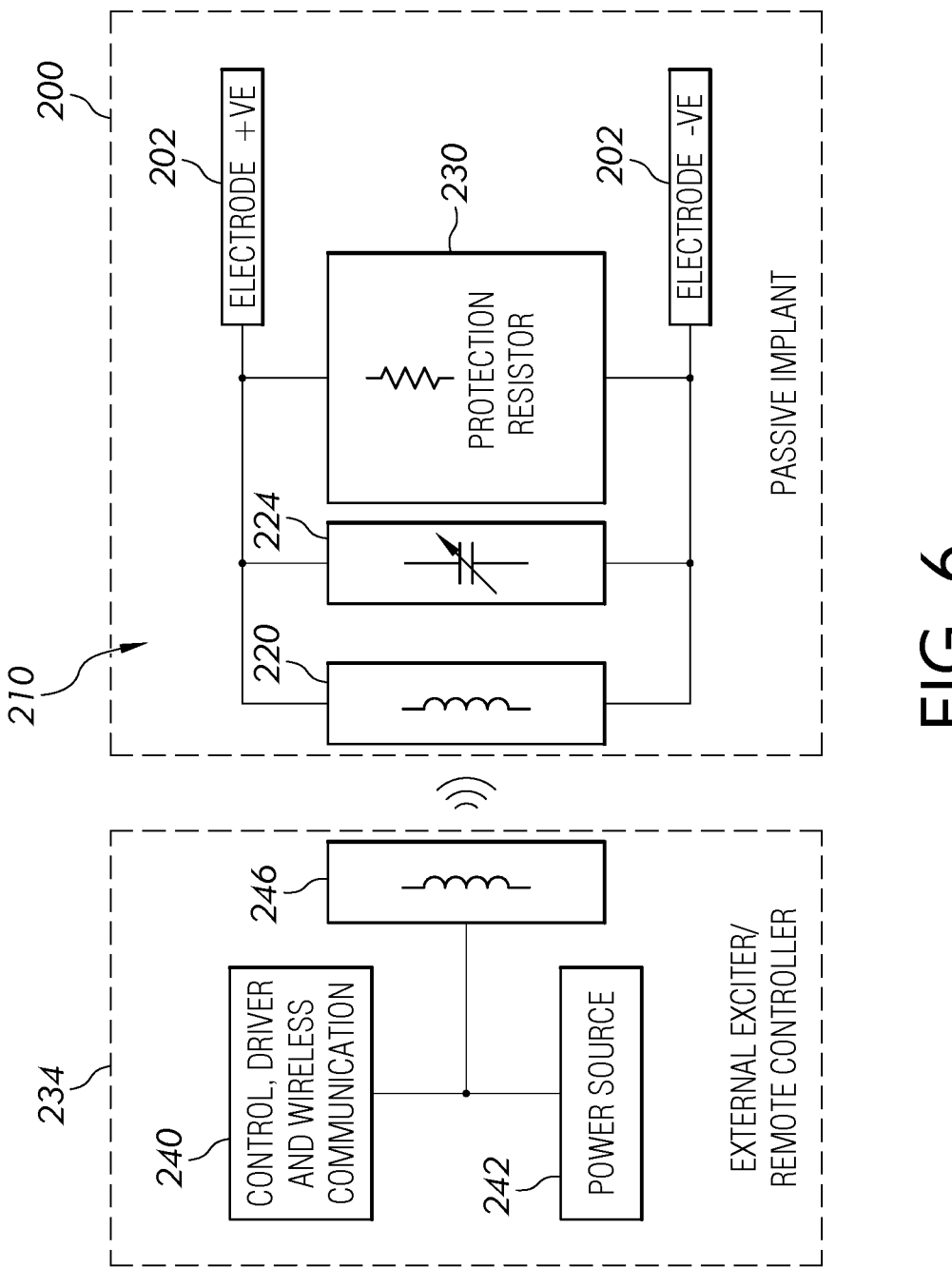
FIG. 6 shows an example neurostimulator that can be coupled to glossopharyngeal nerve of the patient using the method.

Turning to FIG. 6, a specific example of a neurostimulator 200 will now be described that can be implanted using the method described above. The neurostimulator 200 includes one or more electrodes 202 (e.g., cuff electrodes) that can be affixed to the glossopharyngeal nerve 10 such that the electrodes 202 are in electrical communication with the nerve 10. The neurostimulator 200 further includes a neurostimulator circuit 210 for supplying electrical current to the electrodes 202, the circuit 210 including a wireless communication device 220, a charge storage device 224, and a protection resistor/circuit 230. The wireless communication device 220 can comprise a coupling coil, an antenna, or any other device that enables wireless communication between the neurostimulator 200 and another device. In some examples, the wireless communication device 220 can be a receiver that enables one-way communication with another device, or a transceiver that enables two-way communication with the device.

The neurostimulator 200 can be a passive device that delivers electrical stimulation to the glossopharyngeal nerve 10 (via the electrodes 202) according to stimulation parameters that are determined by a current induced in the neurostimulator circuit 210 by an external device. These stimulation parameters can include, for example, the amplitude, frequency, wavelength, waveform, pulse width, pulse phase, and polarity of the electrical stimulation signal.

For example, a remote controller 234 can be located outside of the body in close proximity to the neurostimulator 200. The remote controller 234 can include a control circuit 240, which includes a microprocessor and memory used to store executable code, programming data, stimulation parameters, and other data, which the microprocessor uses to execute the control functions described herein. The control circuit 240 can be configured to utilize a power source 242 to supply current to a coupling coil 246 that displays signal characteristics defined by the desired stimulation parameters. The stimulation parameters can be programmed onto the control circuit 240 via wireless communication, e.g., Bluetooth® or Wi-Fi® radio communication. This programming can be done through any Bluetooth enabled device, such as a smartphone, tablet computer, notebook computer, PC, etc. Other parameters, such as patient information, history, data logging, etc., can also be communicated in this manner.

The control circuit 240 of the remote controller 234 can supply the current to the coupling coil 246 with the desired signal characteristics through, for example, pulse-width modulation ("PWM"). The coupling coil 246, excited by this current, creates an electromagnetic field that displays these same signal characteristics. The wireless communication device (e.g., coupling coil) 220 of the neurostimulator 200 is excited by the field, which causes a current induced therein to have the same or substantially the same signal characteristics. This induced current charges the storage device 224 (e.g., a capacitor), which supplies current to the electrodes 202. The electrodes 202 in turn deliver electrical stimulation with the signal characteristics of the induced current.

In use, the remote controller 234 can control the neurostimulator 200 in an open-loop control scheme. Alternatively, the neurostimulator 200 can include one or more sensors that provide feedback that can be relayed back to the control circuit 240 for closed-loop control. Other devices, such as an external, wearable sensor or implantable sensor can be used to provide feedback. In one specific example, the sensors can be additional electrodes 202 of the neurostimulator 200. The remote controller 234 can apply stimulation via the neurostimulator 200 according to stimulation program(s) stored in the control circuit 240 memory. Stimulation programs can include predetermined, set programs (e.g., firmware) and adaptive, dynamic programs (e.g., software that is configurable/adaptable). The remote controller 234 can select between various programs and/or actively modify a stimulation program according to various inputs received via Bluetooth® from a smartphone, tablet, etc. from a patient or doctor.

It is to be appreciated that other neurostimulators can be implanted by the method 100 without departing from the scope of the disclosure. Broadly speaking, the implanted neurostimulator can be any device that is operable to provide an electrical stimulus to the glossopharyngeal nerve 10.

Turning back to the FIG. 2, once the neurostimulator(s) is/are implanted, the method 100 can include a step 112 of reconnecting any dissected material. Then, the dissected portions of the stylohyoid muscle 20 and digastric muscle 24 can be reconnected to each other with sutures.

Once the dissected material is reconnected, the parotid gland 66 can be swept gently posteriorly and inferiorly back to its normal position, and the method 100 can include a final step 114 of closing the incision. Specifically, the skin portions of opposite sides of the incision can be closed and sutured to complete the method 100.

The method 100 described above provides direct exposure to the glossopharyngeal nerve 10 through a minimally invasive technique. The muscle dissection and location of the glossopharyngeal nerve 10 deep to the styloid process 14 makes this approach favorable for the placement of neurostimulator devices. Another advantage of this technique is a well-concealed scar around the earlobe and low morbidity compared to intracranial approaches.

The invention has been described with reference to the example embodiments described above. Modifications and alterations will occur to others upon a reading and understanding of this specification. Example embodiments incorporating one or more aspects of the invention are intended to include all such modifications and alterations insofar as they come within the scope of the appended claims.

What is claimed is:

1. A method of treating a subject, the method comprising:
   an incision step that includes making an incision adjacent to an earlobe of the subject;
   a dissecting step that includes dissecting one or more anatomical structures of the subject to provide access to a glossopharyngeal nerve of the subject, wherein the dissecting step includes dissecting a stylohyoid muscle and a posterior belly of a digastric muscle of the subject; and
   a coupling step that includes operatively coupling a neurostimulator to the glossopharyngeal nerve.

2. The method of claim 1, wherein the incision has a first portion that extends inferiorly around a base of the earlobe, and a second portion that extends inferiorly from the first portion along a posterior border of a sternocleidomastoid muscle.

3. The method of claim 1, wherein the incision is made through subcutaneous tissue of the subject down to a fascia of the subject.

4. The method of claim 1, wherein after the incision step and before the dissecting step, the method includes a step of sweeping and displacing a parotid gland of the subject to provide access to the stylohyoid muscle and posterior belly.

5. The method of claim 4, wherein the parotid gland is swept anteriorly and superiorly.

6. The method of claim 1, wherein the dissecting step includes dissecting the stylohyoid muscle and the posterior belly, and then dissecting a styloid process of the subject.

7. The method of claim 6, wherein the dissecting step includes performing a blunt dissection of the styloid process.

8. The method of claim 6, wherein the dissecting step includes removing at least a portion of the styloid process from the subject.

9. The method of claim 1, wherein the method includes a step of determining a region of the glossopharyngeal nerve based on at least one landmark from a group consisting of:
   an inferior border of an external auditory canal of the subject,
   a confluence of a mastoid process and a sternocleidomastoid muscle of the subject, and
   a vertex of a mandibular gonial angle of the subject,
   wherein the neurostimulator is coupled within the region of the glossopharyngeal nerve.

10. The method of claim 9, wherein the region of the glossopharyngeal nerve is determined based on at least one predetermined range from a group consisting of:

a first predetermined range that is inferior to the inferior border of the external auditory canal, a second predetermined range that is anterior to the confluence of the mastoid process and the sternocleidomastoid muscle, and a third predetermined range that is deep to the vertex of the mandibular gonial angle.

11. The method of claim 10, wherein:

the first predetermined range is around 3.4 cm, the second predetermined range is around 1.4 cm, and the third predetermined range is around 2.2 cm.

12. The method of claim 10, wherein:

the first predetermined range is at least 3.1 cm and at most 3.9 cm, the second predetermined range is at least 1.2 cm and at most 1.6 cm, and the third predetermined range is at least 1.9 cm and at most 2.5 cm.

13. The method of claim 1, further comprising a reconnecting step that includes reconnecting dissected portions of the stylohyoid muscle and the posterior belly.

14. The method of claim 13, wherein:

after the incision step and before the dissecting step, the method includes a step of sweeping a parotid gland of the subject from an initial configuration to a displaced configuration to provide access to a styloid process, stylohyoid muscle, and posterior belly, and after the reconnecting step, the method includes a step of sweeping the parotid gland from the displaced configuration back to the initial configuration.

15. The method of claim 13, wherein after the reconnecting step, the method includes a closing step of closing the incision.

16. The method of claim 1, wherein the neurostimulator includes at least one electrode that is operatively coupled in electrical communication with the glossopharyngeal nerve.

17. The method of claim 16, wherein the neurostimulator further includes a neurostimulator circuit for supplying electrical current to the at least one electrode, the neurostimulator circuit including a wireless communication device for enabling wireless communication with another device.

18. A neurostimulator for treating a subject, wherein the neurostimulator is configured to be implanted within the subject and coupled to a glossopharyngeal nerve of the subject using the method of claim 1.

19. The neurostimulator of claim 18, the neurostimulator comprising an electrode configured for attachment to a region of the glossopharyngeal nerve, wherein the region is defined by at least one range from a group consisting of:

a first range that is inferior to an inferior border of an external auditory canal of the subject, a second range that is anterior to a confluence of a mastoid process and a sternocleidomastoid muscle of the subject, and a third range that is deep to a vertex of a mandibular gonial angle of the subject.

20. The neurostimulator of claim 19, wherein:

the first range is around 3.4 cm, the second range is around 1.4 cm, and the third range is around 2.2 cm.

* * * * *